(12) United States Patent
Haase et al.

(10) Patent No.: US 10,159,382 B2
(45) Date of Patent: Dec. 25, 2018

(54) SYSTEMS AND METHODS INVOLVING A COMPUTER SYSTEM AND A KITCHEN APPLIANCE

(71) Applicant: Vorwerk & Co. Interholding GmbH, Wuppertal (DE)

(72) Inventors: Corinna Haase, Zurich (CH); Maria Jose Resende, Wollerau (CH); Ramona Wehlig, Horgen (CH); Julius Ganns, Wuppertal (DE); Stefan Hilgers, Essen (DE)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 878 days.

(21) Appl. No.: 14/537,881

(22) Filed: Nov. 10, 2014

(65) Prior Publication Data

US 2015/0164282 A1 Jun. 18, 2015

(30) Foreign Application Priority Data

Nov. 8, 2013 (DE) .......................... 10 2013 112 310

(51) Int. Cl.
*A47J 43/07* (2006.01)
*A47J 36/00* (2006.01)
(Continued)

(52) U.S. Cl.
CPC .......... *A47J 43/0716* (2013.01); *A47J 36/00* (2013.01); *G01N 33/02* (2013.01); *G05B 15/02* (2013.01);
(Continued)

(58) Field of Classification Search
CPC .... G06F 1/1664; G06F 1/1667; G06F 3/0208; G06F 3/0216; G06F 3/048;
(Continued)

(56) References Cited

U.S. PATENT DOCUMENTS

| | | | | |
|---|---|---|---|---|
| 4,649,810 A | * | 3/1987 | Wong | A47J 27/14 222/501 |
| 5,043,860 A | * | 8/1991 | Koether | A47J 27/62 219/494 |

(Continued)

FOREIGN PATENT DOCUMENTS

| | | |
|---|---|---|
| AU | 2010330199 B | 12/2014 |
| CN | 102665496 | 9/2012 |

(Continued)

OTHER PUBLICATIONS

Office Action received in corresponding German application No. 10 2013 112 310.4, dated Aug. 14, 2014, 6 pages.

(Continued)

*Primary Examiner* — Joseph W Drodge
(74) *Attorney, Agent, or Firm* — Knobbe, Martens, Olson & Bear, LLP (57) ABSTRACT

Systems and methods herein relate to arrangements involving a computer system and a kitchen appliance. In one illustrative implementation, such computer system may include a data processing device on which a computer-implemented process is run as a web application, the process being designed to set up a control program for the kitchen appliance, wherein the control program enables an automated preparation of a meal via preparation instruction(s) of the kitchen appliance. Further, in some implementations, the kitchen appliance may comprise a microprocessor, a heatable stirring vessel, and a stirring mechanism located in the stirring vessel, wherein the microprocessor is set up to control the stirring mechanism and/or the heater based on the control program generated.

19 Claims, 2 Drawing Sheets

(51) Int. Cl.
  *G05B 19/04* (2006.01)
  *G05B 15/02* (2006.01)
  *G06F 3/00* (2006.01)
  *G05B 19/042* (2006.01)
  *G01N 33/02* (2006.01)
  *G06F 3/0482* (2013.01)
  *G06F 3/0484* (2013.01)

(52) U.S. Cl.
  CPC ....... *G05B 19/0423* (2013.01); *G06F 3/0482* (2013.01); *G06F 3/04842* (2013.01)

(58) Field of Classification Search
  CPC ............... G06F 3/04842; G05D 23/13; G05D 23/1306; G05D 23/1313; G05D 23/132; A47J 27/00; A47J 27/004; A47J 27/0802; A47J 27/21166; A47J 36/00; A47J 43/00; A47J 43/04; A47J 43/0716; A47J 43/08; A47J 44/00; B01F 15/00; B01F 15/00123; B01F 15/00129; B01F 15/00162; B01F 15/00175; B01F 15/00194; B01F 15/00201; B01F 15/00207; B01F 15/00253; B01F 15/00279; B01F 15/00285; B01F 15/00292; B01F 15/00305; B01F 15/00311; B01F 15/00318; B01F 15/00301; B01F 15/00396; B01F 15/00402; B01F 15/00409; B01F 15/00415; B01F 15/00422; B01F 15/00428; B01F 2215/0026
  USPC ........................ 99/325–338, 348, 468, 486; 366/140–145, 150.1, 151.1, 197, 205, 366/206, 342, 348, 349; 700/11, 12, 275, 700/285, 299, 306
  See application file for complete search history.

(56) References Cited

U.S. PATENT DOCUMENTS

| | | | |
|---|---|---|---|
| 5,373,142 A | 12/1994 | Ohshima et al. | |
| 5,392,695 A * | 2/1995 | Junkel | A21B 7/005 366/145 |
| 5,605,090 A * | 2/1997 | Mantani | A21B 7/005 366/146 |
| 6,549,818 B1 * | 4/2003 | Ali | H05B 6/688 219/720 |
| 6,982,733 B1 * | 1/2006 | McNally | G06F 17/30905 707/E17.121 |
| 7,133,739 B2 * | 11/2006 | Williamson | H04N 21/25891 700/207 |
| 7,197,367 B2 * | 3/2007 | Brinkemper | A47J 31/52 340/4.3 |
| 8,145,854 B1 * | 3/2012 | Lee | A23L 5/00 711/154 |
| 8,766,144 B2 * | 7/2014 | McLoughlin | F24C 7/08 219/391 |
| 9,225,766 B2 * | 12/2015 | Philip | H04L 67/125 |
| 10,004,141 B2 * | 6/2018 | Hackert | A47J 43/046 |
| 2002/0009016 A1 * | 1/2002 | Ancona | A47J 27/62 366/205 |
| 2005/0005266 A1 * | 1/2005 | Datig | G06F 17/279 717/136 |
| 2006/0203610 A1 * | 9/2006 | Bohannon, Jr. | A23G 9/045 366/206 |
| 2008/0140878 A1 * | 6/2008 | Bar-Shalom | G06F 13/28 710/26 |
| 2011/0071651 A1 * | 3/2011 | Law | G05B 19/0426 700/11 |
| 2011/0132201 A1 * | 6/2011 | Richardson | F24C 7/08 99/325 |
| 2012/0054650 A1 * | 3/2012 | Bliss | G05B 19/042 715/764 |
| 2012/0303140 A1 * | 11/2012 | Cox | G05B 15/02 700/17 |
| 2013/0003490 A1 | 1/2013 | Kemker et al. | |
| 2013/0092032 A1 * | 4/2013 | Cafferty | F24C 7/08 99/325 |
| 2013/0264333 A1 * | 10/2013 | Alipour | H05B 6/12 219/621 |
| 2014/0370167 A1 * | 12/2014 | Garden | G06Q 50/12 426/233 |
| 2014/0377417 A1 * | 12/2014 | Martinez | A47J 27/0802 426/231 |

FOREIGN PATENT DOCUMENTS

| | | |
|---|---|---|
| DE | 43 18 206 A1 | 2/1993 |
| DE | 10 2005 040 206 A1 | 2/2007 |
| DE | 10 2005 045 874 A1 | 3/2007 |
| DE | 10 2006 045 874 A1 | 2/2008 |
| DE | 10 2006 060 379 A1 | 6/2008 |
| DE | 10 2007 031372 | 1/2009 |
| DE | 10 2010 060650 | 5/2011 |
| DE | 10 2009 058258 | 6/2011 |
| TW | 201138687 | 1/2009 |
| TW | M401357 | 4/2011 |
| TW | 201138688 | 11/2011 |
| WO | WO 03/031876 A1 | 4/2003 |

OTHER PUBLICATIONS

European Search Report dated Aug. 27, 2015, in European Application No. EP14189976.5 (8 pgs), and Decision to Grant a European Patent dated Jul. 20, 2017 (1 pg); 9 pgs total.

Taiwanese Search Report dated Jan. 8, 2016, in Taiwanese Application No. 103138691 (4 pgs), and English-language translation (5 pgs); 9 pgs total.

* cited by examiner

SYSTEMS AND METHODS INVOLVING A COMPUTER SYSTEM AND A KITCHEN APPLIANCE

CROSS REFERENCE TO RELATED APPLICATION(S)

This application claims priority from German Patent Application No. 10 2013 112 310.4 filed Nov. 8, 2013, which is incorporated herein by reference in entirety.

FIELD/OVERVIEW

Aspects of the innovations herein relate to arrangements involving a computer system and a kitchen appliance. In one illustrative implementation, for example, the computer system may have a data processing device on which a computer-implemented method is run as a web application, said method being designed to set up a control program—which is embodied as a data structure—for the kitchen appliance, wherein the control program enables an automated preparation of a meal by means of a preparation instruction of the kitchen appliance. Further, in some implementations, the kitchen appliance may comprise a microprocessor, a heatable stirring vessel, and a stirring mechanism located in the stirring vessel, wherein the microprocessor is set up to control the stirring mechanism and/or the heater on the basis of the thusly generated control program.

BACKGROUND

Diverse embodiments of kitchen appliances are known from the prior art and are used in the household, in particular, for the preparation of meals. The kitchen appliances often comprise a stirring vessel having a stirring mechanism, which is driven by an electric motor, wherein the drive of the stirring mechanism is provided in the kitchen appliance. In addition, such kitchen appliances, for example the kitchen appliance known by the trade name "Vorwerk-Thermomix", comprise additional devices for the preparation of food items, which are also referred to as cooked items, for example, inter alia, a heating and/or cooking device, a scale, highly diverse embodiments of stirring mechanisms, such as scrapers, etc. Various buttons and switches are provided, in addition to a display, for the purpose of operating the aforementioned devices, by means of which an operator can conveniently control and monitor the preparation of the cooked item.

A recent development within the framework of advancing computerization is a trend of automating the preparation of food items in a kitchen appliance. It is known, for example, that the operator can view preparation instructions on the display of the kitchen appliance, which the operator must then implement in order to prepare the food items, for example by actuating the aforementioned switches or buttons and/or filling the stirring vessel with the ingredients required for the food items.

Such control programs for kitchen appliances are typically stored in a non-volatile memory of the kitchen appliance and can therefore be used immediately after the kitchen appliance is acquired. The reason therefore, inter alia, is that generating the control programs involves a great deal of complexity. This is the case because, in contrast to the generation of other computer programs which, in the worst case scenario of faulty programming, can result in a "blue screen", i.e., a system crash, a faulty control program of a kitchen appliance merely results, in the simplest case, to the prepared food items being inedible. In the worst case, a faulty control program can cause the stirring mechanism to begin moving uncontrollably and disable safety mechanisms, which could result in injury to the operator.

Proceeding therefrom, one aspects addressed by the innovations herein is that of providing an arrangement, by means of which a control program for the automated preparation of a kitchen appliance can be generated and implemented by the kitchen appliance in a particularly simple and reliable manner.

Drawbacks associated with this aspect may be solved by the features of the independent claims. Advantageous embodiments and developments of the invention are described in the dependent claims.

DESCRIPTION OF THE DRAWINGS

The accompanying drawings, which constitute a part of this specification, illustrate various implementations and aspects of the innovations herein and, together with the description, help illustrate the principles of the present inventions. In the drawings.

DETAILED DESCRIPTION OF ILLUSTRATIVE IMPLEMENTATIONS

Reference will now be made in detail to the inventions herein, examples of which are illustrated in the accompanying drawings. The implementations set forth in the following description do not represent all implementations consistent with the present inventions. Instead, they are merely some examples consistent with certain aspects related to the present innovations. Wherever possible, the same reference numbers will be used throughout the drawings to refer to the same or like parts.

According to the innovations herein, the problems noted above may be solved via arrangements involving a computer system and a kitchen appliance. In one illustrative implementation, for example, the computer system may have a data processing device on which a computer-implemented method is run as a web application, said method being designed to set up a control program—which is embodied as a data structure—for the kitchen appliance, wherein the control program enables an automated preparation of a meal by means of a preparation instruction of the kitchen appliance. Further, in some implementations, the kitchen appliance may comprise a microprocessor, a heatable stirring vessel, and a stirring mechanism located in the stirring vessel, wherein the microprocessor is set up to control the stirring mechanism and/or the heater on the basis of the thusly generated control program.

Further, according to implementations herein, the data processing device may be configured to execute the following steps of the method:
 a) entering at least one ingredient of the food item, via an input device,
 b) storing the ingredient in a first data array, via the data processing device, c) entering at least one character sequence that represents a processing sequence of the control program, via the input device, d) storing the character sequence in a second data array, via the data processing device, e) checking to determine whether the character sequence contains a first character, which corresponds to an ingredient, and/or whether the character sequence contains a second character, which corresponds to a preparation instruction, via the data processing device, f) linking the first character that is stored in the second data array to the ingredient stored in the first data array and/or linking the second character that is stored in the second data array to the preparation instruction, via the data processing device, h) checking to determine whether every ingredient entered in step a) has been linked by step f), via the data processing device, k) generating the control program by compiling the linked character sequence, via the data processing device, l) transferring the control program to the kitchen appliance, via the data processing device, m) running the control program, via the microprocessor of the kitchen appliance, and n) controlling the stirring mechanism and/or the heater of the kitchen appliance in accordance with the control program, via the microprocessor, for the automated preparation of the food item.

A further solution of problems noted above relates to a computer-implemented method, which is designed to generate a control program—which is configured as a data structure—of a kitchen appliance, wherein the control program enables an automated preparation of a food item by means of a preparation instruction of the kitchen appliance, and the method has the steps of:

a) entering at least one ingredient of the food item, via an input device, b) storing the ingredient in a first data array, c) entering at least one character sequence that represents a processing sequence of the control program, via the input device, b) storing the character sequence in a second data array, e) checking to determine whether the character sequence contains a first character, which corresponds to an ingredient, and/or whether the character sequence contains a second character, which corresponds to a preparation instruction, f) linking the first character that is stored in the second data array to the ingredient stored in the first data array and/or linking the second character that is stored in the second data array to the preparation instruction, h) checking to determine whether every ingredient entered in step a) has been linked by step f).

Innovations herein may, therefore, implement an entirely new approach by virtue of the fact that an arrangement for the automated generation and implementation of a control program for the automated preparation of a food item by means of a kitchen appliance is proposed. The method, which is preferably configured as a web application and can be run in a web browser used by the operator, initially enables the input of the ingredients of the desired food item to be prepared, via the input device, for example a keyboard, in step a), wherein the ingredient can be "onion", for example.

The ingredient that is entered via the input device is then stored in a first data array. The data array is preferably part of a database, for example a database programmed in SQL or Oracle. Provided that the food item to be prepared comprises a plurality of ingredients, as is usually the case, steps a) and b) can be carried out repeatedly, which is preferable, until all the ingredients have been entered and stored in the first data array. In this case, an individual data field in the first data array is preferably assigned to every individual ingredient.

According to some implementations, an important aspect of the innovations herein may relate, according to step c), to a character sequence being entered by the computer-implemented method, for example by means of the aforementioned keyboard in this case as well. The character sequence is a processing step of the control program, wherein the character sequence is preferably entered as plain text and is stored in a second data array by means of step d). Since the preparation of a food item often comprises a plurality of processing steps, which is also referred to in totality as a recipe, the steps c) and d) are preferably carried out repeatedly until all the processing steps have been entered by the input device and, preferably, have each been stored in an individual data field of the second data array. To this end, the second data array is preferably provided in the database, as is the first data array. Given that the processing steps can be entered as plain text, the computer-implemented method can be implemented particularly easily by the operator. An input entered by an operator can read, for example, "Place onions into the stirring vessel and run the stirring mechanism for 5 seconds at speed 7".

Next, a check is performed in step e) to determine whether the character sequence contains a first character, which corresponds to an ingredient, and/or whether the character sequence contains a second character, which corresponds to a preparation instruction. According to the aforementioned example, the character sequence initially contains the ingredient "onion" and the preparation instructions "5 seconds" and "speed 7". The computer-implemented method investigates the character sequence during step e), preferably initially by means of a parser, in order to obtain—via fragmentation and/or conversion of the character sequence—a format that is usable for the further processing, thereby making it possible to carry out the check claimed in step e), for example by performing a character comparison.

Once the character sequence or, preferably, all the entered character sequences have been checked according to step e), the first character stored in the second data array, which was previously entered by means of step e), is linked, in step f), to the ingredient stored in the first data array, which was entered by means of step e), and/or the second character stored in the second data array, which was also entered by means of the preceding step e), is linked to the preparation instruction.

The linking preferably takes place within a database, wherein a link can also be implemented by means of a hyperlink or a comparable option. As a result, the character sequence, which can be entered in advance as plain text, is linked to the previously entered ingredients of the food item and/or of the preparation instructions of the kitchen appliance by means of the link, thereby making it possible to derive the control program for the automated preparation of the food item, in a format suitable for computer processing, from the thusly-obtained link of ingredients to processing steps or preparation instructions.

Finally, a consistency check may be carried out in step h) to determine whether every ingredient entered in step a) has been linked by means of the step f), that is, whether the control program contains a link for every ingredient. It is thereby possible to ensure that all ingredients have actually been taken into account in the control program to be generated. In addition, it can also be possible to enter not only ingredients but also further instructions, for example serving instructions, which can then be linked in the same manner, thereby permitting the aforementioned consistency check to be carried out for the serving instructions as well.

As a result, the method under discussion enables an automated and particularly simple generation of a control program of a kitchen appliance, which, in a further step after generation and transfer to the kitchen appliance, enables the automated preparation of the food items on the kitchen appliance.

According to a preferred embodiment, the method further comprises the step of: g) repeating step f) until all the first characters of the character sequence, which correspond to an ingredient, are linked to an ingredient stored in the first data array, and/or until all second characters of the character sequence, which correspond to a preparation instruction, are linked to a preparation instruction. Preferably, step f) is repeated for the number of times that corresponds to the number of different ingredients that were entered in step a), thereby ensuring that every ingredient in the character sequence has been entered.

If it is determined in the repetition of step f) that not all of the entered ingredients have been linked, for example because not all of the ingredients were entered in the entered character sequence or in the entered character sequences in step e), the method can output an error message and prompt the operator to enter additional character sequences, for example. In this case, the operator can be shown, on a display, those ingredients that have not yet been entered in the character sequences by means of step e).

According to a further preferred embodiment, the method further comprises the step i), that is, a check to determine whether every second character found in step e) is linked to a preparation instruction. In this case as well, it can be provided that the method outputs an error message in order to enable the operator to edit the character sequence entered in step c) and/or to enter additional character sequences into the input device. In any case, this step enables another consistency check to be carried out to determine whether all the preparation instructions have actually been correctly entered and linked.

According to a very particularly preferred embodiment, a selection menu for selecting the ingredient entered in step a) and/or for selecting the preparation instruction of the kitchen appliance is provided according to step c'). Particularly preferably, the provision according to step c') takes place during step c). The operator can be provided with a particularly simple option within the framework of a selection menu, for example a scroll-down menu, by means of which the operator can easily select the previously entered ingredients, optionally also in portions, for example by clicking on the relevant ingredient.

According to systems and methods herein, an operator may select, via the selection menu, the preparation instructions of the kitchen appliance (which may be previously-defined), for example in terms of speed, temperature or duration, of the stirring mechanism, the heater, etc., which are typically dependent on the designated kitchen appliance on which the control program is intended to be run. Furthermore, the computer-implemented method can comprise variables that define the preparation instructions that are basically available and, therefore, selectable on a certain model of the kitchen appliance. In this context, it is very particularly preferable for the preparation instruction to be selectable from the parameters of time, speed, temperature, weighing and/or steam cooking. Provided the kitchen appliance can be manufactured with different stirring mechanisms, stirring vessels and/or expansions of the aforementioned components, additional parameters can result therefrom.

According to a further preferred embodiment, the quantity of the ingredient and the unit of measure of the quantity are entered, for each ingredient, in step a). The quantity can be a numerical value, for example, whereas the unit of measure can be expressed as "gram", "teaspoon", "ml", or the like. According to a further preferred embodiment, the method comprises a further checking step, by means of which a check is carried out to determine whether the entered quantity can be processed by the kitchen appliance, that is, for example, whether the entered quantity is larger than the stirring vessel of the kitchen appliance. For this case, it can be provided that the method automatically outputs an error message and the operator is prompted to correct the quantity. It can also be provided that the total quantity of all ingredients that are input is checked with respect to the maximum quantity that can be processed by the kitchen appliance. In order to ensure simple handling, the quantity and/or the unit of measure can be selected from a menu, wherein it can also be provided that the quantity and/or the unit of measure can be entered by means of a keyboard as the input device.

According to a further preferred embodiment, it can also be provided that the method comprises the step f') of outputting the character sequence with a depiction of the linked characters, and/or the step j) of providing an editing mechanism for editing the character sequence that was output. The linked characters are preferably depicted by means of a visual emphasis of the link, for example by means of underlining and/or bold type. The editing mechanism, which can be embodied as an activatable menu function, provides the operator with the possibility to revise, add to, and/or delete character sequences that may have been incorrectly entered. In any case, the aforementioned embodiments result in a very user-friendly operation of the method.

Once the operator has entered all the ingredients and all the character sequences by means of the input device, and the method has successfully carried out all links and checks, the next steps are, preferably, the steps of k) generating the control program by compiling the linked character sequence, and step l) transferring the control program to the kitchen appliance. As mentioned above, the first data array and the second data array are preferably stored in a database, wherein the processing steps of the control program were entered by means of the character sequence and the appropriate linking according to step f). Once the aforementioned steps have been successfully carried out, the control program is preferably present in the database, for example as a recipe for automatic implementation.

In order to then execute the control program on the kitchen appliance, a compilation step may initially be utilized or required, according to the proposed step k). The kitchen appliance preferably comprises a microprocessor, wherein the compilation preferably takes place such that the compiler creates a code that can be executed by the microprocessor of the kitchen appliance. The control program is preferably transferred to the kitchen appliance in a wired or wireless manner via a network, or, for example, by means of a USB stick or a similar medium. After the control program has been transferred to the kitchen appliance, the microprocessor of the kitchen appliance can run the compiled control program for the automated preparation of the food item, for example after receipt of a start instruction by the operator.

Problems addressed by aspects of the present innovations may furthermore be solved by the kitchen appliance comprising a data processing device, wherein the data processing device is designed to run a control program that has been generated according to the above-described method. Further preferably, the kitchen appliance comprises a stirring vessel and a stirring mechanism located in the stirring vessel, wherein the stirring vessel can be heated and the stirring mechanism and/or the heater can be controlled by means of the control program. The kitchen appliance can comprise additional components or aspects for the preparation of the food item, for example a scale, wherein these additional components can also be controlled by means of the control program.

Problems addressed via the innovations herein may further be solved by a computer system comprising a data processing device, wherein the data processing device is configured such that the above-described processing may be executed on the data processing device. To this end, the data processing device may be configured as a computer that is known from the prior art, wherein, particularly preferably, the method is executed by the data processing device as a web application. In this case, the method, which is executed on a single data processing device, can be carried out by a plurality of different operators at different geographical locations. Further preferably, the computer-implemented method is programmed in a programming language such as Java, thereby making it possible for the data processing device to execute the method as a web application in a particularly simple manner.

The problem addressed by the invention is further solved by a digital storage medium having control signals that can be read out electronically, wherein the control signals can interact with a programmable computer system such that an above-described method is carried out. The problem is further solved by a computer program product having a program code, which is stored on a machine-readable carrier, for executing the method when the program code is run on a data processing device. Finally, the problem is solved by a computer program having a program code for executing the method when the program runs on a data processing device.

The inventions are described in greater detail in the following with reference to the attached drawings and on the basis of an illustrative embodiment.

Figure 1:
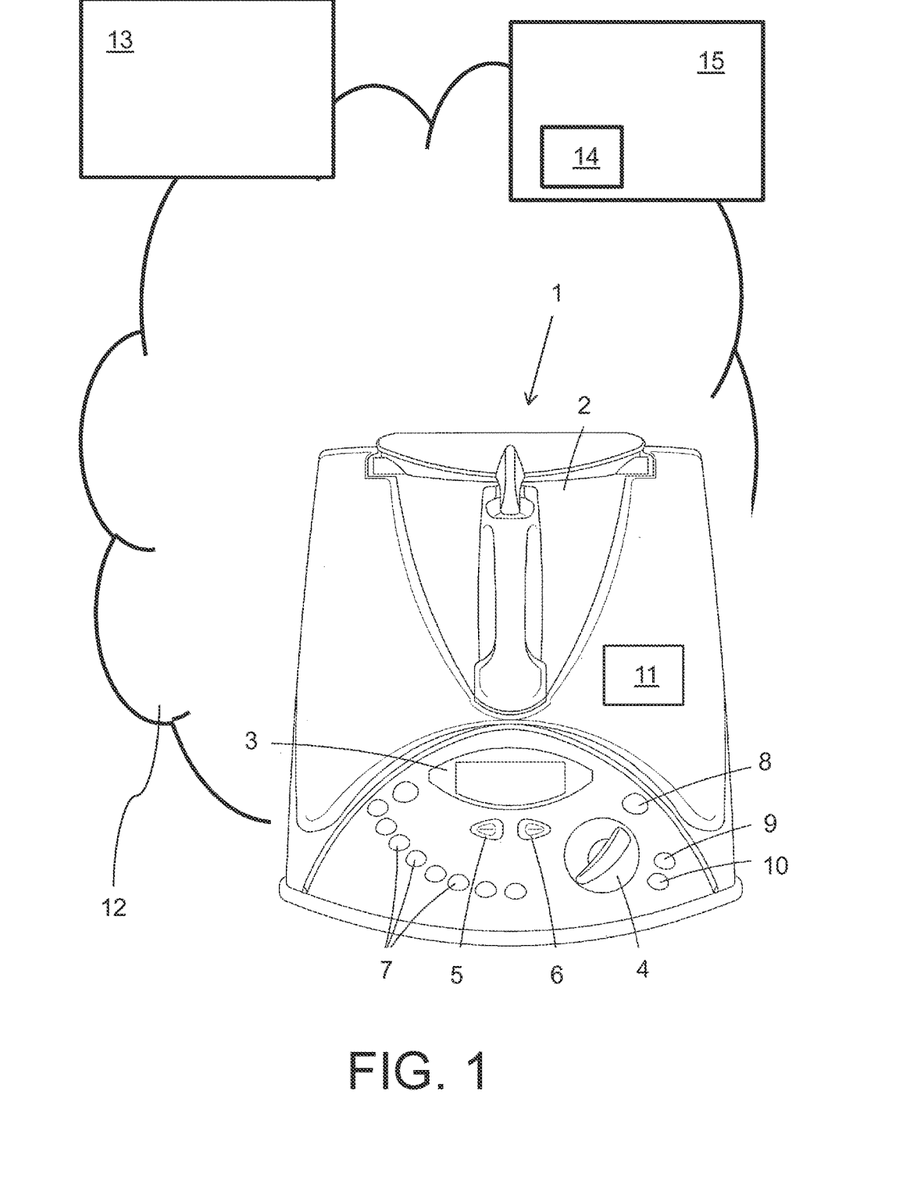
FIG. 1 illustrates a kitchen appliance comprising a data processing device for executing the processes herein, consistent with certain aspects related to the present innovations.

FIG. 1 shows a kitchen appliance 1, which is also known as a "Vorwerk-Thermomix".

The kitchen appliance 1 comprises a stirring vessel 2, which has a non-visible stirring mechanism disposed at the bottom of the stirring vessel 2. The stirring vessel 2 is heatable, for example via an electric resistance heater provided on the bottom of the stirring vessel 2. A display 3 is provided on the kitchen appliance 1, which displays, inter alia, the speed of rotation of the stirring mechanism and the temperature of the resistance heater.

In addition, various control elements are provided for the manual preparation of food items, for example a rotary selector switch 4 for setting a stirring mechanism speed, actuating buttons 5, 6 for setting the time, buttons 7 for preselecting the temperature of the resistance heater, and further switches 8 to 10, by means of which a further functionality of the kitchen appliance 1 can be set, for example a turbo function, a weighing function, or the like.

In order to manually prepare a food item, the ingredients of the food item are placed into the stirring vessel 2 and then the function of the kitchen appliance 1 that is appropriate for preparing the food item is selected by means of the actuating buttons 5, 6, 7 and/or the switchs 8 to 10. In addition to the aforementioned manual preparation of the food item, the kitchen appliance 1 comprises a microprocessor 11, which controls the automated preparation of the food item by reference to a control program. The control program can be transferred to the kitchen appliance 1 from a data processing device 13, which is configured as a computer, by means of a network 12, which is implemented as a wireless network in the present case.

A computer-implemented method is carried out on the data processing device 13 as a web application, which is designed to generate the control program of the kitchen appliance 1 such that the food item can be prepared in an automated manner by means of a preparation instruction of the kitchen appliance by reference to the completed control program, which has been transferred to the kitchen appliance 1.

Figure 2:
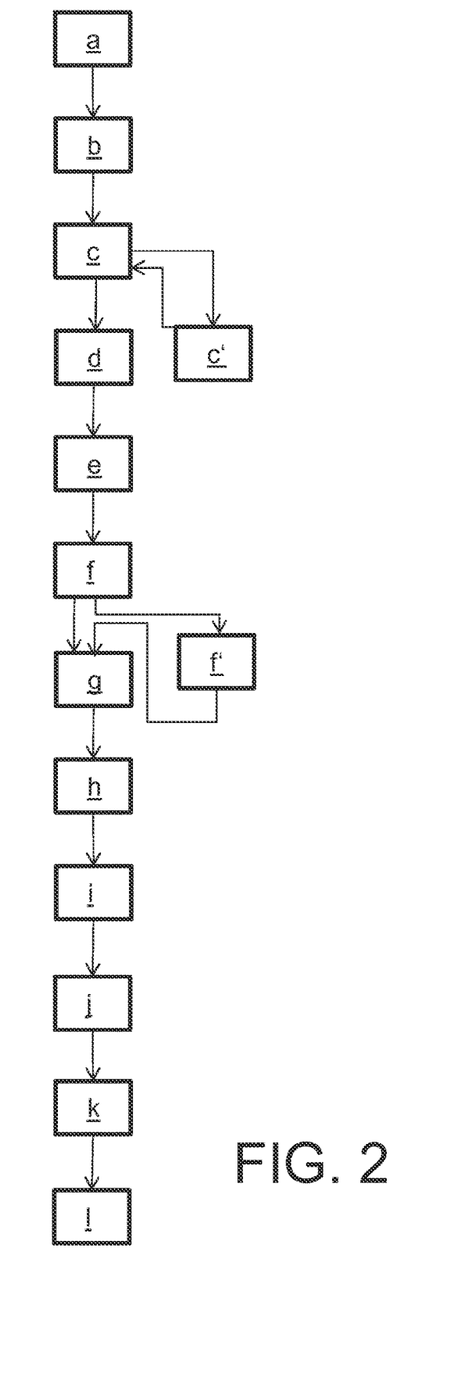
FIG. 2 illustrates an illustrative flow chart for executing the processes herein, consistent with certain aspects related to the present innovations.

The method, which is depicted by reference to a flow chart in FIG. 2, comprises various steps for this purpose, wherein these steps can be carried out in succession and are described in detail in the following:

In step a), the at least one ingredient of the food item is entered by means of an input device 14, for example by means of a keyboard of a computer 15 belonging to an operator who has called up, on his computer 15, the web application that is run on the data processing device 13. In addition to the ingredient, which is entered as "onion" in the present case, the quantity of the ingredient is also entered, for example "200", and the unit of measure of the quantity, for example "g" for grams. As a result, "200 g onion" has been entered.

After the ingredient is entered, the ingredient is stored, in step b), in a first data array on the data processing device 13, that is, in a database running on the data processing device 13. The operator repeats steps a) and b) until all the ingredients of the food item to be prepared have been entered.

In step c), at least one character sequence that represents a processing step of the control program is entered. This means that the operator enters plain text into the web application by means of the input device 14, which is configured as a keyboard, wherein said plain text represents a processing step of the control program. In the present case, this plain text is "Place onion into the stirring vessel and run the stirring mechanism for 5 seconds at speed 7". According to step d), the character sequence is stored in a second data array of the database.

In order to simplify the input of the character sequence, the web application comprises a selection menu, by means of which the operator can select the ingredients entered in step a) and a preparation instruction of the kitchen appliance, for example by means of a computer mouse in a pop-down menu or selection menu.

Within the scope of the invention, the expression "preparation instruction" is intended to mean a parameter of the kitchen appliance 1, by means of which the preparation of the food item can be controlled, for example time, i.e., how long the stirring mechanism or the resistance heater should act on the ingredient, speed, for example of the stirring mechanism, temperature, for example of the resistance heater, weighing, for example a weighing function of the kitchen appliance 1, and/or steam cooking by means of the stirring vessel 2. As initially discussed, such preparation instructions can also be set manually by means of the rotary selector switch 4, the actuating buttons 5, 6, 7, and the switches 8 to 10.

In step e), the computer-implemented method performs a check to determine whether the character sequence contains a first character, which corresponds to an ingredient, and/or whether the character sequence contains a second character, which corresponds to a preparation instruction. To this end, the previously entered plain text is first broken down by a parser and converted into a format that can be processed by the data processing device 13, thereby making it possible to compare the divided components of the character sequence with the ingredients, which were previously entered in step a), and with the preparation instructions. In the present case, the result of the check is that the ingredient "onion" is identified and the preparation instruction "5 seconds" and "speed 7" is ascertained.

The first character and the second character ascertained by means of step e) are then linked to the ingredients and the preparation instructions in step f). This means that the characters that are stored in the second data array and that were ascertained in the previous step are linked to the ingredient stored in the first data array, and the second characters that are stored in the second data array and that were ascertained in the previous step are linked to the respective preparation instruction. Such linking takes place by adding a hyperlink to the character sequence, which, according to step f'), can be output on a display of the computer 15 with a representation of the linked character.

According to step g), step f) is now repeated until all the first characters of the character sequence, which correspond to an ingredient, are linked to an ingredient stored in the first data array, and/or until all second characters of the character sequence, which correspond to a preparation instruction, are linked to a preparation instruction.

Next, a check is carried out in step h) to determine whether every ingredient entered in step a) has been linked by step f). In addition, a check is carried out in step i) to determine whether every second character that is found in step e) is linked to a preparation instruction. In other words, a consistency check is carried out by means of the aforementioned steps to determine whether every previously entered ingredient and every preparation instruction have been linked.

Next, the operator is given the opportunity once more, in step j), to edit the character sequence that was entered or that was output by step f'), for example if a change was made to a preparation instruction or a recipe step.

Finally, in step k), the control program is generated by compiling the linked character sequences into a control program that can be run by the microprocessor 11 of the kitchen appliance 1 and can then be transferred, by means of step 1), from the data processing device 13 to the kitchen appliance 1 by means of the network 12.

As disclosed herein, implementations and features of the invention may be implemented through computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe components such as software, systems and methods consistent with the present innovations may be implemented with any combination of hardware, software and/or firmware. Moreover, the above-noted features and other aspects and principles of the present inventions may be implemented in or via various environments. Such environments and related applications may be specially constructed for performing the various processes and operations according to the inventions or they may include a general-purpose computer or computing platform selectively activated or reconfigured by code to provide the necessary functionality. Certain processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

The systems and methods disclosed herein may be implemented as a computer program product, i.e., a computer program tangibly embodied in an information carrier, e.g., in a machine readable storage medium or element, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computing element or on multiple computing elements at one site or distributed across multiple sites and interconnected by a communication network.

It is to be understood that the foregoing description is intended to illustrate and not to limit the scope of the inventions herein. Other implementations are within the scope of the present inventions.

LIST OF REFERENCE CHARACTERS

| | |
|---|---|
| kitchen appliance | 1 |
| stirring vessel | 2 |
| display | 3 |
| rotary selector switch | 4 |
| actuating buttons | 5, 6, 7 |
| switch | 8, 9, 10 |
| microprocessor | 11 |
| network | 12 |
| data processing device | 13 |
| input device | 14 |
| computer | 15 |

The invention claimed is:
1. A meal preparation arrangement comprising:
a computer system; and
a kitchen appliance comprising a microprocessor;
wherein the computer system has a data processing device that is configured to execute computer-implemented instructions via a Web application that is configured to perform a computer-implemented method via at least one network connecting the computer system and the kitchen appliance, the data processing device being configured to automatically generate and implement a control program for the kitchen appliance, the control program designed as a data structure generated by the Web application on the data processing device for execution by the microprocessor of the kitchen appliance, wherein the control program is configured to perform an automated preparation of a meal by executing meal preparation instructions via the kitchen appliance;

wherein the kitchen appliance further comprises a heatable stirring vessel, and a stirring mechanism located in the stirring vessel, wherein the microprocessor is configured to control the stirring mechanism and/or a heater of the stirring vessel based on the control program; and wherein the data processing device is configured to execute the following steps of the method:

a) entering at least one ingredient of the food item, via an input device, b) storing the ingredient in a first data array, via the data processing device, c) entering at least one character sequence that represents a processing sequence of the control program, via the input device, d) storing the character sequence in a second data array, via the data processing device, e) automatically checking to determine whether the character sequence contains a first character, which corresponds to an ingredient, and/or whether the character sequence contains a second character, which corresponds to a preparation instruction, via the data processing device, f) linking the first character that is stored in the second data array to the ingredient stored in the first data array and/or linking the second character that is stored in the second data array to the preparation instruction, via the data processing device, f') outputting the character sequence on a display that includes a depiction of the linked characters, wherein the depiction includes a further graphical visual emphasis of alphanumeric text that constitutes the link, h) checking to determine whether every ingredient entered in step a) has been linked by step f), via the data processing device, j) providing an editing mechanism for editing the character sequence that was output, the editing mechanism comprising a processor, an input device including a keyboard to enter characters of character sequences, as well as a display that displays activatable menu functions, and error messages, the character sequences being output, the characters being entered by the keyboard, and a depiction of the character sequences including the visual emphasis of the linked characters, wherein the editing mechanism provides visual display and a consistency check of character sequences and links and is configured to allow a user to provide keyboard inputs that selectively revise, add to and/or delete the character sequences and thereby also alter resulting food processing steps associated with respective food preparation actions that change based on the edited character sequences, including at least one parameter for operation of the appliance selected from the group consisting of speed, temperature, timing, duration, weighing, cooking and stirring operation of the appliance, k) generating the control program by compiling the edited linked character sequence, via the data processing device, l) transferring the control program to the kitchen appliance, via the data processing device, and m) running the control program, via the microprocessor of the kitchen appliance, and n) controlling the stirring mechanism and/or the heater of the kitchen appliance in accordance with the control program, via the microprocessor, for the automated preparation of a food item of the meal.

2. The arrangement according to claim 1, wherein the data processing device is further configured to execute a step of:

g) repeating step f) until all the first characters of the character sequence, which correspond to an ingredient, are linked to an ingredient stored in the first data array, and/or until all second characters of the character sequence, which correspond to a preparation instruction, are linked to a preparation instruction.

3. The arrangement according to claim 2, wherein the data processing device is further configured to execute a step of:

i) checking to determine whether every second character found in step e) is linked to a preparation instruction.

4. The arrangement according to claim 3, wherein the data processing device is further configured to execute a step of:

c') providing a selection menu, via the display, for selecting the ingredient entered in step a) and/or for selecting the preparation instructions of the kitchen appliance.

5. The arrangement according to claim 4, wherein the quantity of the ingredient and/or a unit of measure of the quantity are entered, via the editing mechanism, for each ingredient, in step a).

6. The arrangement according to claim 5, wherein the kitchen appliance further comprises a scale, and the microprocessor is set up to control the scale by reference to the generated control program.

7. The arrangement according to claim 1, wherein the data processing device is further configured to execute a step of:

i) checking to determine whether every second character found in step e) is linked to a preparation instruction.

8. The arrangement according to claim 1, wherein the data processing device is further configured to execute a step of:

c') providing a selection menu for selecting the at least one ingredient entered in step a) and/or for selecting the preparation instructions of the kitchen appliance.

9. The arrangement according to claim 1, wherein the preparation instructions are selected from actions concerning parameters of time, speed, temperature, weighing and/or steam cooking.

10. The arrangement according to claim 1, wherein the quantity of the ingredient and/or a unit of measure of the quantity are entered, for each ingredient, in step a).

11. The arrangement according to claim 1, wherein the kitchen appliance further comprises a scale, and the microprocessor is set up to control the scale by reference to the generated control program.

12. The arrangement according to claim 1, wherein, in step e), the checking process comprises an initial analysis followed by subsequent character comparison, wherein the initial analysis includes the character sequence being initially analyzed using a parser that obtains, via decomposition and/or conversion of the character sequence, a format configured for use in subsequent processing, wherein the format is configured to enable performance of the subsequent character comparison of the checking process via the character comparison.

13. A computer-implemented method for operating a meal preparation arrangement comprising a computer system and a kitchen appliance, the computer system having a data processing device that automatically generates and implements a control program for the kitchen appliance and on which computer-implemented instructions are executed as a Web application that performs the method via at least one network connecting the computer system and the kitchen appliance, the method comprising:

a) entering at least one ingredient of the food item, via an input device, b) storing the ingredient in a first data array, via the data processing device, c) entering at least one character sequence that represents a processing sequence of a control program, via the input device, d) storing the character sequence in a second data array, via the data processing device, e) automatically checking to determine whether the character sequence contains a first character, which corresponds to an ingredient, and/or whether the character sequence contains a second character, which corresponds to preparation instructions, via the data processing device, f) linking the first character that is stored in the second data array to the ingredient stored in the first data array and/or linking the second character that is stored in the second data array to the preparation instructions, via the data processing device, f') outputting the character sequence on a display that includes a depiction of the linked characters, wherein the depiction includes a further graphical visual emphasis of alphanumeric text that constitutes the link, h) checking to determine whether every ingredient entered in step a) has been linked by step f), via the data processing device, j) providing an editing mechanism for editing the character sequence that was output, the editing mechanism comprising a processor, an input device including a keyboard to enter characters of character sequences, as well as a display that displays activatable menu functions, and error messages, the character sequence being output, the characters being entered by the keyboard, and a depiction of the character sequences including the visual emphasis of the linked characters, wherein the editing mechanism provides visual display and a consistency check of character sequences and links and is configured to allow a user to provide keyboard inputs that selectively revise, add to and/or delete the character sequences and thereby also alter resulting food processing steps associated with respective food preparation actions that change based on the edited character sequences, including at least one parameter for operation of the appliance selected from the group consisting of speed, temperature, timing, duration, weighing, cooking and stirring operation of the appliance, k) generating the control program by compiling the edited linked character sequence, via the data processing device, l) transferring the control program to the kitchen appliance, via the data processing device, and m) running the control program, via the microprocessor of the kitchen appliance, and n) controlling a stirring mechanism and/or a heater of the kitchen appliance in accordance with the control program, via the microprocessor, for automated preparation of a food item of the meal.

14. The method of claim 13, further comprising:

g) repeating step f) until all the first characters of the character sequence, which correspond to an ingredient, are linked to an ingredient stored in the first data array, and/or until all second characters of the character sequence, which correspond to a preparation instruction, are linked to a preparation instruction.

15. The method of claim 13, further comprising:

i) checking to determine whether every second character found in step e) is linked to a preparation instruction.

16. The method of claim 13, further comprising:

c') providing a selection menu for selecting the at least one ingredient entered in step a) and/or for selecting the preparation instructions of the kitchen appliance.

17. The method of claim 13, wherein the control program is configured to provide for the quantity of the ingredient and/or a unit of measure of the quantity to be entered, for each ingredient, in step a).

18. The method of claim 13, wherein the kitchen appliance further comprises a scale, and the microprocessor is set up to control the scale by reference to the control program.

19. The method of claim 13, wherein, in step e), the checking process comprises an initial analysis followed by subsequent character comparison, wherein the initial analysis includes the character sequence being initially analyzed using a parser that obtains, via decomposition and/or conversion of the character sequence, a format configured for use in subsequent processing, wherein the format is configured to enable performance of the subsequent character comparison of the checking process via the character comparison.

\* \* \* \* \*